US00PP26318P2

(12) United States Plant Patent
Jack

(10) Patent No.: US PP26,318 P2
(45) Date of Patent: Jan. 19, 2016

(54) ***CHAMELAUCIUM* PLANT NAMED 'STRAWBERRY SURPRISE'**

(50) Latin Name: ***Chamelaucium* hybrid**
Varietal Denomination: Strawberry Surprise

(71) Applicant: Brian Jack, Coorow (AU)

(72) Inventor: Brian Jack, Coorow (AU)

(73) Assignee: WAFEX PTY LTD, Perth (AU)

( * ) Notice: Subject to any disclaimer, the term of this patent is extended or adjusted under 35 U.S.C. 154(b) by 101 days.

(21) Appl. No.: 13/999,206

(22) Filed: Jan. 29, 2014

Related U.S. Application Data

(60) Provisional application No. 61/849,560, filed on Jan. 29, 2013.

(51) Int. Cl.
*A01H 5/02* (2006.01)

(52) U.S. Cl.
USPC ..... Plt./229

(58) Field of Classification Search
USPC ..... Plt./229
See application file for complete search history.

(56) References Cited

PUBLICATIONS

"Exciting Range of New Waxflower Varietes for the Middle East," Gulf Agriculture, Jul.-Aug. 2011, pp. 16-18.*

* cited by examiner

*Primary Examiner* — Susan McCormick Ewoldt
(74) *Attorney, Agent, or Firm* — Penny J. Aguirre

(57) ABSTRACT

A new cultivar of *Chamelaucium*, 'Strawberry Surprise' that is characterized by its flowers that are a rich pink in color, its flower buds that are hot pink in color, its flower clusters that bloom from axels up to 12 cm the length of the stems (longer than typical), and its late blooming period.

1 Drawing Sheet

Botanical classification: *Chamelaucium* hybrid.
Variety denomination: 'Strawberry Surprise'.

BACKGROUND OF THE INVENTION

The present invention relates to a new and distinct cultivar of *Chamelaucium* of hybrid origin, 'Strawberry Surprise'. The new cultivar will be referred to hereafter by its cultivar name, 'Strawberry Surprise'. 'Strawberry Surprise' is a new cultivar of waxflower, an evergreen shrub grown for use as a landscape plant and is particularly suited for cut flower use.

The Inventor discovered the new cultivar of *Chamelaucium* in September of 2005 as a naturally occurring whole plant mutation in a production field at a nursery in Coorow, Australia. The parent plants are unknown, however, the parents are thought to be *Chamelaucium uncinatum* 'Purple Pride' (not patented) and *Chamelaucium* 'Sweet Georgia' (not patented, hybrid origin) based on the characteristics of the new cultivar and their proximity in the field to 'Strawberry Surprise'.

Asexual propagation of the new cultivar was first accomplished by the Inventor by stem cuttings in Coorow, Australia in September of 2005. Asexual propagation by stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Strawberry Surprise' as a unique cultivar of *Chamelaucium*.

1. 'Strawberry Surprise' exhibits flowers that are a rich pink in color.
2. 'Strawberry Surprise' exhibits flower buds that are hot pink in color.
3. 'Strawberry Surprise' exhibits flower clusters that bloom from axels up to 12 cm the length of the stems (longer than typical).
4. 'Strawberry Surprise' exhibits a late blooming period.

'Strawberry Surprise' can be most closely compared to the probable parent plants 'Purple Pride' and 'Sweet Georgia'. 'Purple Pride' differs from 'Strawberry Surprise' in having smaller flowers that are pale purple-pink in color, in having fewer flower clusters, and in flowering earlier. 'Sweet Georgia' differs from 'Strawberry Surprise' in having larger flowers that are white in color, in having shorter flower heads, and in flowering earlier. 'Strawberry Surprise' can also be compared to the cultivar 'Mullering Brook' (not patented). 'Mullering Brook' differs from 'Strawberry Surprise' in having larger flowers that are lighter pink in color, and in having fewer flower clusters.

BRIEF DESCRIPTION OF THE DRAWINGS

The accompanying colored photographs illustrate the overall appearance and distinct characteristics of the new cultivar. The photographs were taken of a two year-old plant of the new cultivar as grown outdoors in a field in Coorow, Australia.

The photograph in FIG. 1 provides a view of cut flowering stems in a vase of 'Strawberry Surprise'.

Figure 1:
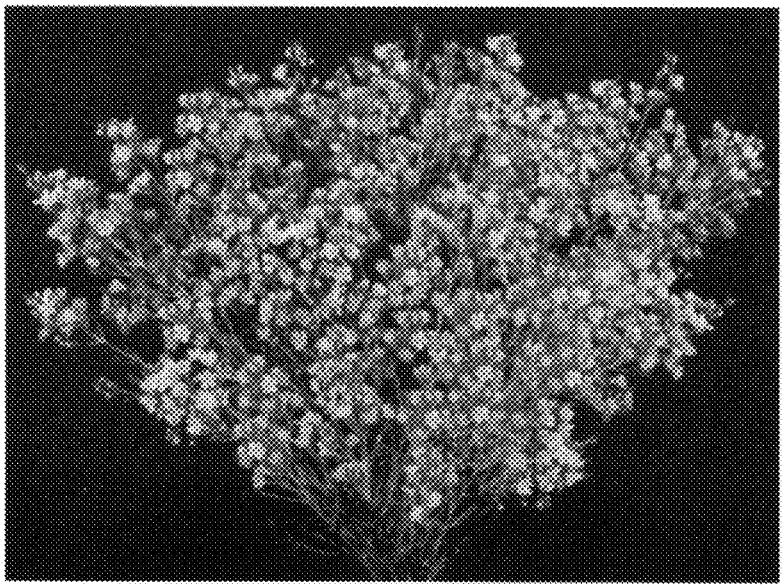
Figure 2:
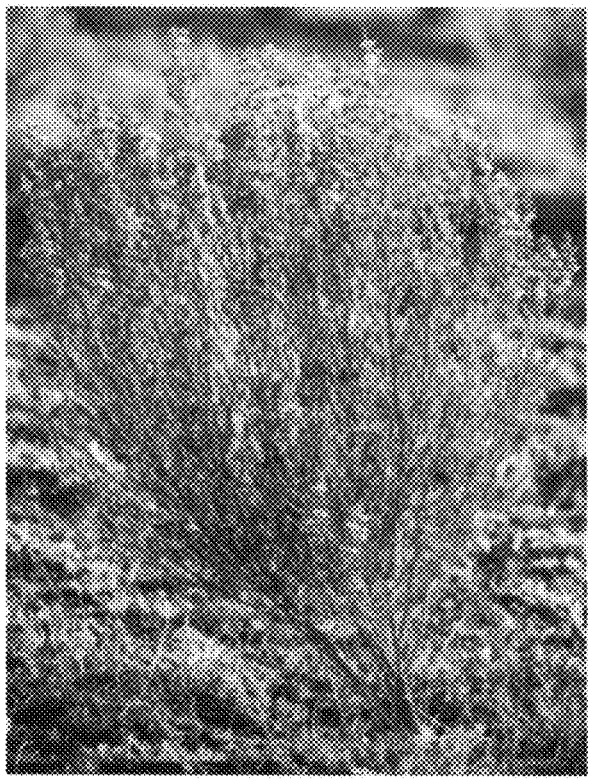

The photograph in FIG. 2 provides a view of the plant habit of 'Strawberry Surprise'.

The colors in the photographs are as close as possible with digital photography techniques available, the color values cited in the detailed botanical description accurately describe the colors of the new *Chamelaucium*.

DETAILED BOTANICAL DESCRIPTION

The following is a detailed description of two year-old plants the new cultivar as grown outdoors in a field in Coorow, Australia. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Blooms for 4 to 6 weeks in late winter to late spring in Coorow, Australia.

*Plant type*.—Evergreen shrub.

*Plant habit*.—Upright, semi-open.

*Height and spread*.—1.52 m in height and 1.2 m in spread.

*Hardiness*.—At least in U.S.D.A. Zones 9 to 11.

*Diseases*.—No resistance or susceptibility to diseases has been observed.

*Environmental stresses*.—Grows well in hot climates, withstands intense sunlight, drought resistant.

*Propagation*.—Stem cuttings.

*Growth*.—Vigorous.

*Roots*.—Strong thick well-branched primary roots with fibrous secondary roots.

*Rooting*.—About 15 to 30 days in well drained media a greenhouse with rooting hormone (IBA) at 3000 ppm and bottom heat of 15° C. in strong natural sunlight in autumn, rooted cutting will fill a 3-inch tube container in about 60 days in temperatures of 25° to 30° C. in well drained neutral media.

Branch description:

*Stem color*.—New growth; blend of 144A and N167B, mature wood; a blend of 198A and 164B.

*Stem surface*.—New growth; glossy and glabrous, mature wood; smooth and dull.

*Branching*.—3 basal branches, up to 20 lateral branches per main stem, an average of 4 tertiary branches per lateral branch.

*Stem size*.—Average of 3 mm in width and 55 cm in length.

Foliage description:

*Leaves*.—Simple, linear in shape, opposite arrangement, average of 1 cm in length and 1 mm in width, internode length up to 1 cm, attachment sessile, glabrous on entire surface, color: new foliage all surfaces; blend of 143A with base N144B, mature foliage both surfaces; 137A with apex and base 183A.

Inflorescence description:

*Inflorescence type*.—Clusters on terminals and upper axils of main stems and lateral and tertiary branches.

*Inflorescence size*.—Clusters bloom up to 12 cm in length on stem.

*Inflorescence number*.—Average of 10 clusters per lateral branch.

*Flower number*.—Average of 4 per cluster.

*Flower fragrance*.—None.

*Inflorescence longevity*.—About 5 weeks in the landscape.

*Longevity as a cut flower*.—7 to 12 days.

*Harvest production period for cut flowers*.—Up to 8 weeks.

*Harvest production yield*.—20 to 60 stems on a 2 year-old plant, 70 to 100 stems on plants 3 years old or more.

*Flower type*.—Cup shaped with base of corolla fused to calyx.

*Flower size*.—Average of 1.1 cm in diameter and 1 cm in depth.

*Peduncles*.—Average of 1.4 cm in length and 0.8 mm in diameter, color; 144B at apex and 164C at base, surface is dull and smooth.

*Pedicels*.—Average of 6 mm in length and 1 mm in diameter, color 144B, surface is glabrous and smooth.

*Flower buds*.—Globose-obovate in shape, an average of 7 mm in length and 5 mm in width, operculum color; 157C, bud color once operculum sheds; N74B to N74C.

*Calyx*.—Campanulate and narrowing to tube (hypanthium), average of 7 mm in length and width, including tube portion 4 mm in length and width.

*Sepals*.—5, fused with free obtuse apex, an average of 6 mm in depth and 3 mm in width, margin entire, color of upper and lower surface 144A with free apex 67A to 67C occasionally suffused with 59B, both surfaces are glabrous and waxy.

*Petals*.—5, orbicular in shape, not overlapping, slightly cupped, margin entire, base cuneate and fused to calyx and nectary, apex is obtuse to truncate, average of 5 mm in length and 5.5 mm in width, color of opening flowers upper and lower surface; NN155C heavily suffused with 72A to 72C, color of mature flowers; 72A to 72B, surface glabrous and waxy on upper and lower surface.

*Nectaries* (*centers*).—Slightly cupped in shape, 5 mm in diameter and 2 mm in depth, a blend of 144A to 144B and 34C.

Reproductive organs:

*Pistils*.—1, stigma is an average of 0.5 mm in diameter, 199D in color with hairs an average of 0.5 mm in length, style is an average of 5 mm in length and 1 mm in width (narrows at apex) and 155A in color with apex 72A in color, ovary is conical-shaped, 3.5 mm in length and width and 144A suffused with 59B in color.

*Stamens*.—An average of 10, with 10 infertile stamenoids arranged between stamens, filaments are triangular in shape, up to 1.5 mm in length and 1 mm in width and NN155C in color, anthers are an average of 0.5 mm in width and 177C in color, pollen not discernable, stamenoids; triangular in shape, average of 1.5 mm in length, NN155C with apex 72A in color.

*Fruit and seed*.—Fruit production has not been observed to date.

It is claimed:

1. A new and distinct cultivar *Chamelaucium* plant named 'Strawberry Surprise' as herein illustrated and described.

* * * * *